United States Patent [19]

Zeng et al.

[11] Patent Number: 4,957,114
[45] Date of Patent: Sep. 18, 1990

[54] DIAGNOSTIC APPARATUS FOR INTRINSIC FLUORESCENCE OF MALIGNANT TUMOR

[76] Inventors: Kun Zeng; Jinrong Wu; Sen Yang; Zhenfen Yu, all, of No. 77 Jiangning Lu; Jiude Zhu, No. 111 Zun Yi Lu, all of Shanghai, China

[21] Appl. No.: 212,630

[22] Filed: Jun. 28, 1988

Related U.S. Application Data

[63] Continuation of Ser. No. 843,950, Mar. 25, 1986, abandoned.

[30] Foreign Application Priority Data

Apr. 1, 1985 [CN] China .................................. 85100424

[51] Int. Cl.$^5$ ................................................ A61B 6/00
[52] U.S. Cl. .......................................... 128/665; 606/3
[58] Field of Search ............... 128/633, 634, 653, 665, 128/303.1, 395, 397, 398; 606/3, 15

[56] References Cited

U.S. PATENT DOCUMENTS

| Re. 31,815 | 1/1985 | Alfano | 128/665 |
|---|---|---|---|
| 3,313,290 | 4/1967 | Chance et al. | 128/633 |
| 4,213,462 | 7/1980 | Sato | 128/634 |
| 4,295,470 | 10/1981 | Shaw et al. | 128/634 |
| 4,449,535 | 5/1984 | Renault | 128/634 |
| 4,541,438 | 9/1985 | Parker et al. | 128/664 |
| 4,556,057 | 12/1985 | Hiruma et al. | 128/634 |
| 4,576,173 | 3/1986 | Parker et al. | 128/634 |
| 4,648,892 | 3/1987 | Kittrell et al. | 128/634 |

FOREIGN PATENT DOCUMENTS

| 135576 | 7/1960 | U.S.S.R. | 128/665 |
|---|---|---|---|
| 0787044 | 12/1980 | U.S.S.R. | 128/397 |

OTHER PUBLICATIONS

Alfano et al., "Laser Induced Fluorescence Spectroscopy from Native Cancerous and Normal Tissue", IEEE Journal of Quantum Electronics, vol. QE-20, No. 12, Dec. 1984, pp. 1507-1511.

Schuette et al., "The Design and Operation of a Dual--Beam Long-Focal-Length Fluorometer for Monitoring the Oxidative Metabolism in Vivo", Med & Biol Eng., Mar. 1976, pp. 235-238, vol. 14, No. 2.

Dislich, "Optical Fiber Technology" IEEE Press, 1973, pp. 94-99.

*Primary Examiner*—Ruth S. Smith
*Attorney, Agent, or Firm*—Pennie & Edmonds

[57] ABSTRACT

This invention relates to a diagnostic apparatus and particularly to an apparatus for the diagnosis of malignant tumor and the method of using the apparatus for diagnosis. The apparatus employs an ultraviolet light source with an emitting waveband of 3000A-4000A. Light from the light source is transmitted through a bundle of quartz optic fibers to the surface of the tumor, whether benign or malignant, to stimulate it, which then generates a specific intrinsic fluorescence spectrum. The intrinsic fluorescence spectrum reflected from the surface of the tumor is transmitted by a second bundles of glass fibers placed near it to a color resolution means, then processed by a scanning means and a circuit means, and displayed recorded by a display recording means. The display may be a graphic presentation of the intrinsic fluorescence spectrum of the tumor that is tested. If the graphic presentation displayed includes a single peak within the range of the blue color band, it indicates that the tumor being tested is benign. If however, a second peak appears within the range of the red color band of the graphic presentation it is a characteristic peak of malignancy, indicating the existence of a malignant tumor. The presence of the red color can be established by eye rather than a complex color resolution system.

7 Claims, 3 Drawing Sheets

DIAGNOSTIC APPARATUS FOR INTRINSIC FLUORESCENCE OF MALIGNANT TUMOR

This is a continuation of application Ser. No. 843,950 filed Mar. 25, 1986, now abandoned.

FIELD OF INVENTION

This invention relates to a diagnostic apparatus and particularly to an apparatus for use in the diagnosis of a malignant tumor and to the method of using the apparatus for diagnosis.

BACKGROUND ART

A paper entitled "The Study of the Analysis of Laser Stimulated Fluorescence Spectrum of the Digestive System and the Nature of it's Fluorescent Material," relating to the use of an argon laser having a wavelength of 5145 A as a light source has appeared in the *Journal of the Japanese Association for Digestive Organ Endoscopy*, Vol. 26, 8 Aug. 1984. The paper, more particularly, demonstrates the use of such an argon laser as a light source for directly illuminating an isolated specimen from the body and analyzing the intrinsic fluorescence spectrum generated by the light source to determine whether a malignant tumor exists in the isolated specimen. It has been found, however, that the method cannot be used satisfactory to diagnose gastric cancer, and its accuracy in the diagnosis of cancer of the large intestine was found to be only 30%. This is because the blue-green light of the argon-ion laser is visible light that superimpose upon the visible light waveband of the fluorescence spectrum generated by its stimulation on the isolated speciment, which is liable to lead to erroneous diagnosis. Moreover, the research studies embodied in this paper are only in the stage of experimentation, and up to this time no complete apparatus has achieved a satisfactory diagnosis of a malignant tumor.

DISCLOSURE OF THE INVENTION

It is a primary object of the invention to provide a diagnostic apparatus and method to improve the accuracy of diagnosis of a malignant tumor.

It is another object of the invention to provide an apparatus capable of rapid operation, and one which may be used simply and in a non-invasive manner to clinically diagnose malignant tumors of various kinds, as well as provide a method of using the apparatus diagnostically.

A further object of the invention is to provide a diagnostic apparatus that uses a high energy light source with specific wavelengths in order to increase the sensitivity of the diagnosis.

Additional objects, advantages and other novel features of the invention are set forth in the description that follows, and other objects, advantages and features will become apparent to those skilled in the arts to which the invention pertains.

The objects and advantages of the invention may be realized and attained through improvement of the light source and light transmitting means for stimulating and transmitting the intrinsic fluorescence of a tumor. Particularly, an improved diagnostic apparatus is provided to stimulate the intrinsic fluorescence of a tumor and determine according to the spectrum and color of said fluorescence whether the tumor is benign or malignant. The apparatus provides an ultraviolet light source with an emitting waveband of 3000 A–4000 A. Light from the light source is transmitted through a bundle of quartz optical fibers to the surface of the tumor whether benign or malignant, to stimulate it, which then generates a specific intrinsic fluorescence spectrum. The intrinsic fluorescence spectrum generated by the tumor is transmitted by a second bundle of ordinary glass fibers placed near it to a color resolution system.

The spectrum can be processed by an automatic scanning system and an electric system, and both displayed and recorded by a display recording system.

The display may be a graphic presentation of the intrinsic fluorescence spectrum of the tumor that is tested. If the graphic presentation displayed includes a single peak within the range of the blue color band, it indicated that the tumor being tested is benign. If, however, a second peak appears within the range of the red color band of the graphic presentation, the second peak is representative of tissue demonstrating the existence of malignancy.

As compared with the prior art, the apparatus of the invention advantageously uses a near ultraviolet light source with an emitted wavelength of 3000 A–4000 A, rather than an argon-ion laser. Since the energy of the stimulating beam is greatly increased and the emitted wavelength of the light source is closer to the absorbed peak value of 3400 A±200 A by a malignant tumor, the apparatus provides increased sensitivity and therefore accuracy of diagnosis. More importantly, since the near ultraviolet waveband emitted by the light source is invisible, while the intrinsic fluorescence stimulated by the light source is visible, the intrinsic fluorescence spectrum from the tumor is a visible spectrum without any superpositioning of the light spectrum from the light source. This has the effect of significantly increasing the accurate of the diagnosis of a malignant tumor by the apparatus of the invention. To this end the apparatus is able to diagnose malignant tumors 1-2 mm in thickness in the mucosa or submucosa. This capability is of great importance in early diagnosis of cancer.

The apparatus embodies soft, flexible fiber optics cables to transmit stimulating light from the light source to the surface of the tumor tissue, and to transmit the intrinsic fluorescence from the tumor to the color resolution system. The apparatus is easy to operate and may be used to diagnose malignancy on a body surface or within a body cavity. Thus, the flexible fiber optics cables may function as an endoscope and this also can be used to guide the surgeon to define the position and the extent of a malignancy exposed in a field of operation.

The apparatus is simple and non-invasive in operation and attains high diagnostic accuracy in use. The apparatus may be used widely to diagnose a malignancy of a biological speciment or in general investigation. Four hundred and six cases of various kinds of malignancies were verified through use of the apparatus at the Central Hospital of Changning District, Shanghai, China, the Shanghai Municipal Tumor Hospital, and the Obstetrical and Gynecological Hospital of Shanghai, China, a hospital affiliated with the Shanghai First Medical College. The apparatus provided a demonstrated accuracy of 90 percent.

A preferred embodiment of the invention and the best mode suited to carry out the invention are illustrated in the drawings and further described as the description continues. As may be understood, however, the invention is capable of other difference embodiments, and its several details are capable of modification all without departing from the spirit of the invention. Accordingly the drawings and the description that follow should be regarded as illustrative in nature.

BRIEF DESCRIPTION OF THE PREFERRED EMBODIMENT

Figure 1:
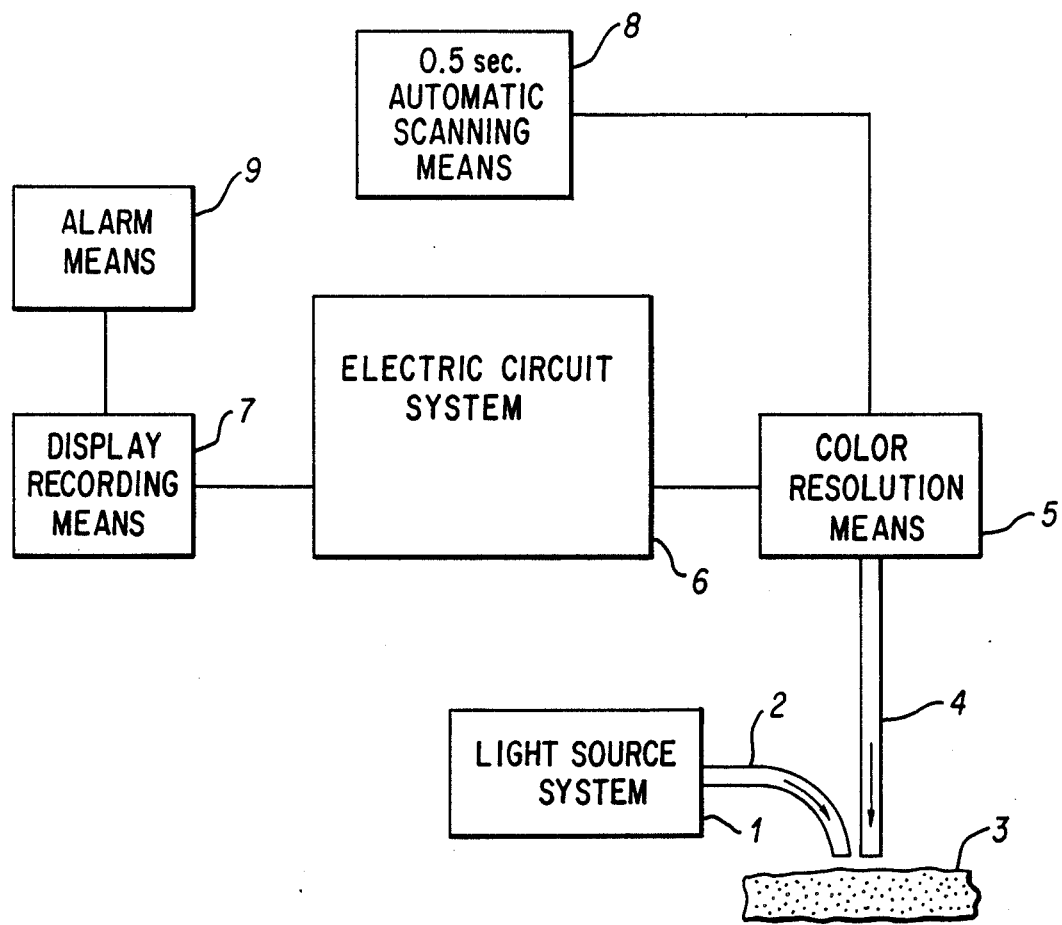
FIG. 1 is a block drawing of the diagnostic apparatus of the invention.

With reference to FIG. 1, the diagnostic apparatus for intrinsic fluorescence of malignant tumor includes a light source system (1) for emitting near ultraviolet light having a wavelength of 3000 A–4000 A. A cable (2) comprised of a bundle of quartz optical fibers is connected to the light source to transmit the light emitted from the light source to the tissue (3) be tested. A second cable (4) of ordinary glass optical fibers is located in a position relative to the tissue to receive the intrinsic fluorescence of the living tissue stimulated by the near ultraviolet light. The cable (4) for transmitting the intrinsic fluorescence from the simulated living tissue is connected to a color resolution system (5) such a conventional prism or grating.

As shown in the figure, the output of the color resolution system can be fed into an electric circuit system (6) (usually a conventional photomultiplier tube and associate amplification circuitry). The electric circuit system, as is conventional in optical systems, can control a display recording system (7) and an automatic scanning system (8) which, in tune can control the color resolution system with a 0.5 second scan. If desired, an alarm system (9) can be connected to the display recording system.

Figure 2:
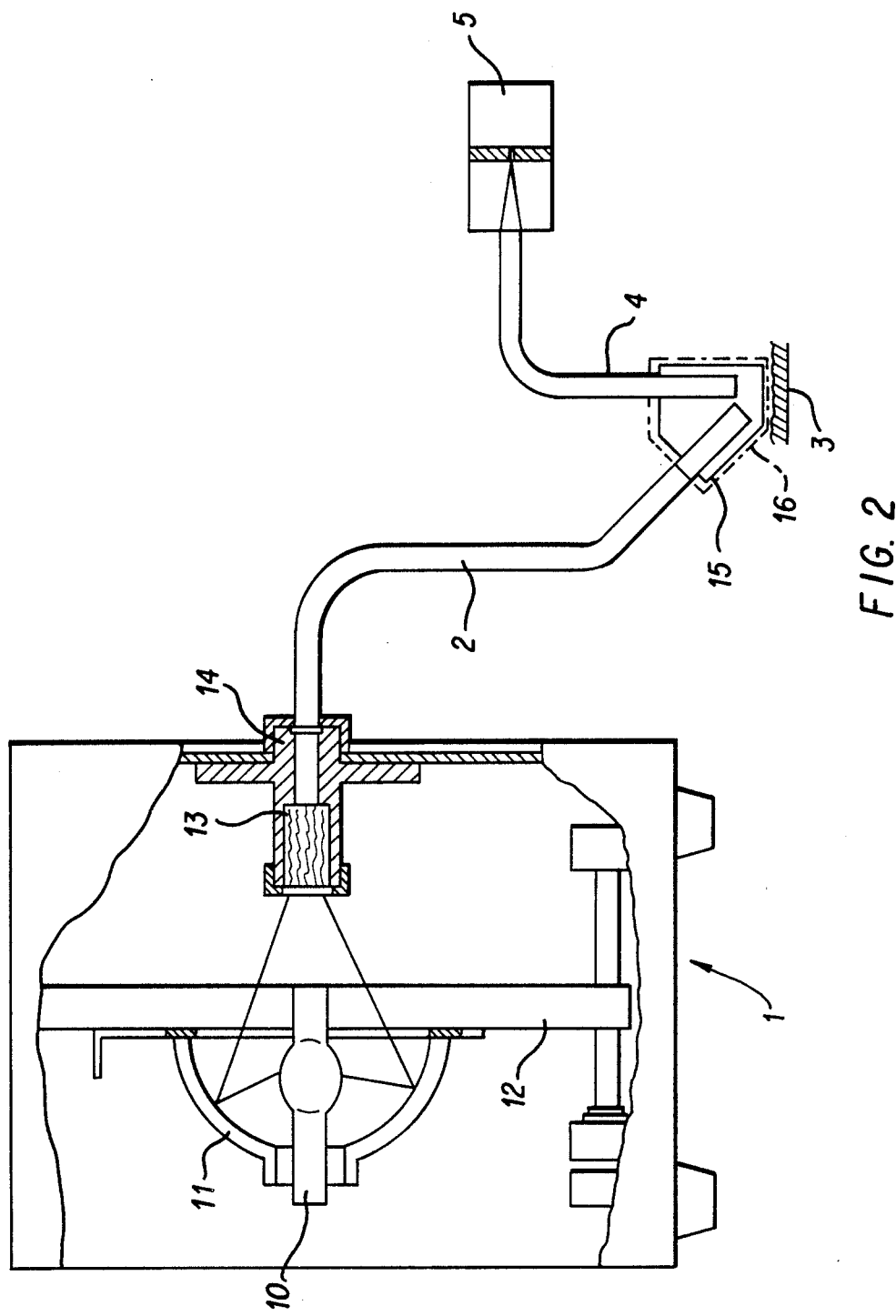
FIG. 2 is a diagrammatic view of the structure of light source system and light transmitting system.

Referring to FIG. 2, light source system (1) includes a mercury lamp (10) and reflecting bowl (11). Both the mercury lamp and the reflecting bowl are fixed on a stand (12) within a housing. The reflecting bowl reflects the light emitted from the mercury lamp toward the center of an ultraviolet filter which forms an excellent, single stimulating light of 3650 A closing to the best functioning waveband 3400±200 A. The focus of the light toward the center of a stack of plates is carried out through adjustment of adjustable stand (12). The stacked plates comprising the ultraviolet filter may include from four to twelve superposed plates in number, and each plate may have a thickness of 1-2 mm.

As indicated, the cables (2) and (4) comprise a light transmitting system for transmitting the stimulating light from the light source system to the surface of the tumor (3) and the intrinsic fluorescence of the tumor to the color resolution system. The system may be formed as multibundles and the quartz optical fibers of cable (2) comprise a low energy consuming multibundle.

With continued reference to FIG. 2, the incident or efferent end of the optical fibers of cable (2) from which stimulating light impinges on the surface of the tissue emanates is preferably at an acute angle to the surface of the tumor, while the reflective or afference end of the optical fibers of cable (4) for receiving the intrinsic fluorescence is located perpendicular to the surface of the tumor. The angle of the incident end of cable (2) to the surface (3) and the reflective end of cable (4) is about 45°. A fix stand (15) both locates and fixes the position of the ends of the cable thereby to control the angle between the ends, and the distance to the surface of the living tissue to be tested. The distance from the surface of the tumor to the ends of the optic fibers should be about 2 to 10 mm. A shade (16) similar in size to that of the fix stand tightly covers the surface of the fix stand. In operation of the apparatus, the lower end of the shade is firmly attached to the surface of the tumor to be tested. The shade should be changed after each use to avoid cross infection as may otherwise result from repeated connection of the same shade with living tissue.

The near ultraviolet light of 3000 A–4000 A wavelength emitted from the light source system (1) is transmitted by the cable (2) of quartz optical fibers to the surface (3) of the tumor. The tumor may comprise normal tissue or malignant tissue. The light stimulates the tissue to emit an intrinsic fluorescence. The generated intrinsic fluorescence is transmitted by the cable (4) of ordinary glass optical fibers to a color resolution system (5). The color resolution system may be controlled through a 0.50 second automatic scanning system (8). An electric circuit system (6) may be used to process the signal for display and to record the intrinsic fluorescence spectrum.

Figure 3:
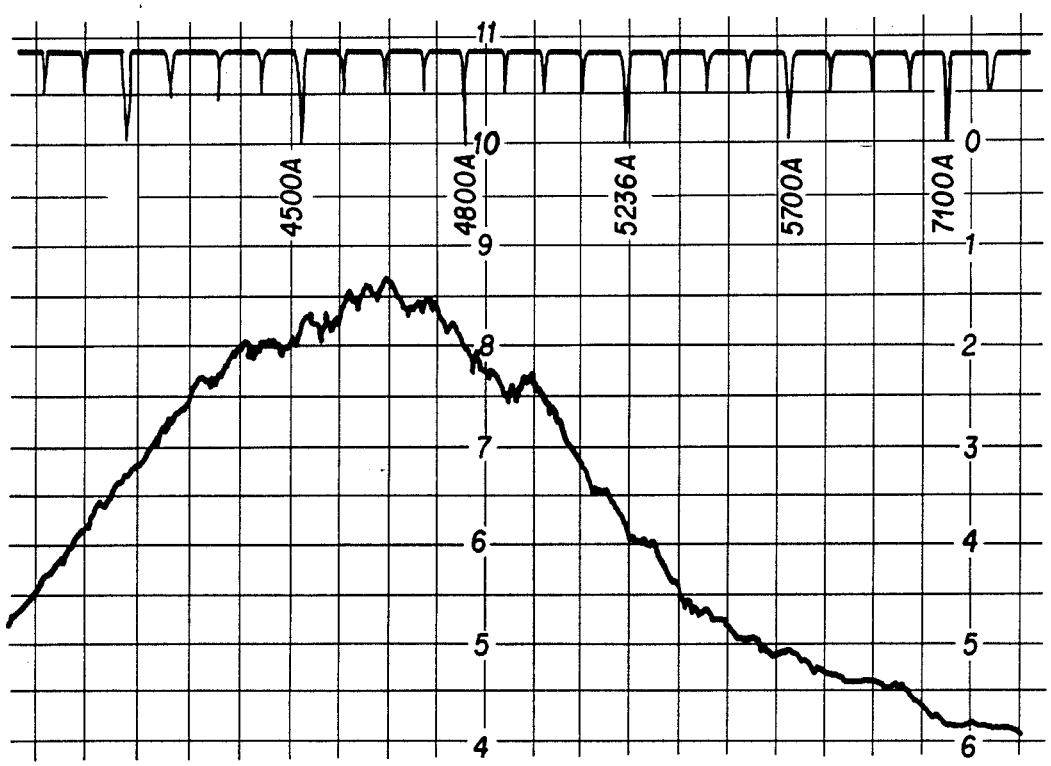
FIG. 3 illustrates the intrinsic fluorescence spectrum of living tissue that is normal.
Figure 4:
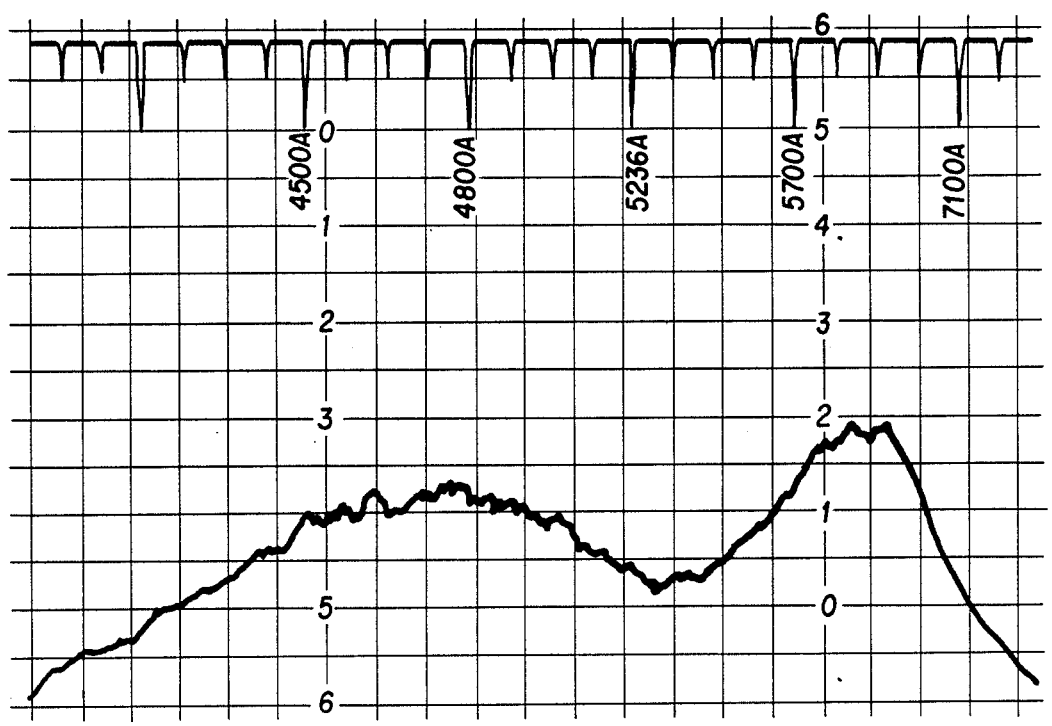
FIG. 4 illustrates the intrinsic fluorescence spectrum of living tissue that is cancerous.

FIG. 3 illustrates the intrinsic fluorescence spectrum of normal, living tissue. Normal, living tissue is represented by a spectrum graph with one peak within the blue color waveband at 4500 A–4800 A. FIG. 4, on the other hand, illustrates the intrinsic fluorescence spectrum of malignant, living tissue. In this figure, in additional to the peak with the blue color wavelength at 4500 A–4800 A, there also appears a characteristic peak within the red color waveband at 6000 A–6900 A representing malignant tissue.

A mercury lamp (10) provides advantages in use in the apparatus of the invention. To this end, the mercury lamp is simpler in construction that other ultraviolet light sources, is more easily used in operation, and provides convenient maintenance, at low cost. The mercury lamp may also be used over extended periods of time. As an alternative, however, the light source may comprise an ultraviolet laser with the light from the light source being similarly transmitted to the surface of the living tissue to stimulate its intrinsic fluorescence. The advantage of the ultraviolet laser is that the energy of the laser is greater and it has higher efficiency in stimulating the intrinsic fluorescence of the living tissue. Thus, the demand of an electric circuit system (6) for processing the intrinsic florescence may be reduced. The advantages, however, may be counterbalanced by higher cost of apparatus with an ultraviolet laser.

The ultraviolet laser may comprise any one of a nitrogen laser, krypton laser, xenon laser and ultraviolet excimer laser apparatus.

Another alternative form of the present invention envisions that the incident end of cable (2) and the reflective end of cable (4) may be made into a coaxial construction. This construction has the effect of diminishing the contact surface between the living tissue and the optic fibers, and it also decreases the space occupied by optical fibers. The alternative form of the invention may be resorted to in use of the apparatus as an endoscope for deep entry into and diagnosis of an inner cavity of the body. The length of the coaxial construction will be determined by the depth within the body cavity that is to be reached for diagnosis.

According to the coaxial construction, the optical fibers of cable (2) for transmitting stimulating light are made of low energy consumption quartz glass, and the optic fibers of cable (4) for transmitting intrinsic fluorescence of living tissue are made of ordinary optical glass. The optical fibers of cable (2) may be in the form of multibundles or the cable may comprise a single optical fiber having a diameter of 300u–600u. The optical fibers of cable (4) may also be in the form of bundles that surround the optical fibers of cable (2). In addition, the bundles of optical fibers of cable (2) and (4) may be arranged in an alternating arrangement in the coaxial construction. It has been found that the coaxial construction optical fiber is less effective than the noncoaxial construction of optical fibers. Therefore, the coaxial construction should be used only when demand dictates its use.

According to the invention, the wave spectrum of the intrinsic fluorescence of the living tissue is displayed and recorded in the diagnoses of the presence or absence of a malignancy in the tissue tested. Alternatively, in the simplest use of the overall method of testing, the color of the intrinsic fluorescence emitted by the stimulated tissue may be observed directly by eye. The invention employs a source of ultraviolet light having an emitting wavelength of 3000 A–4000 A, preferably 3400±–200 A. Since the wavelength of stimulated intrinsic fluorescence of malignant tissue lies within the 6000 A–6900 A waveband of red color, the tested living tissue illuminated by the nearby ultraviolet light source through cable (2) may be observed by naked eye. If the intrinsic fluorescence emitted from the tested living tissue is a visible red or of reddish color the immediate diagnosis is that a malignant tumor exists in the living tissue that is tested.

Other modifications and variations of the invention may be made within the scope of the invention and teachings, all as defined by the scope of the appended claims.

We claim:

1. An apparatus for the diagnosis of malignant tumors comprising:
   (a) means for generating near ultraviolet light having a frequency range of 3000° A to 4000° A;
   (b) light transmission means composed of a bundle of optical fibers for transmitting the light to the surface of a tumor in order to stimulated intrinsic fluorescent light emission from said tumor;
   (c) further light transmission means composed of a second bundle of optical fibers having an incident end and an efferent end for transmitting the stimulated intrinsic fluorescence light emitted by the tumor wherein the incident end of said second bundle of optical fibers has means to maintain the incident end of the fibers in a position perpendicular to the surface of the tumor;
   (d) color resolution means connected to the efferent end of said second bundle of optical fibers for processing the intrinsic fluorescent light output therefrom in order to determine the presence of light of a frequency of 6000° A to 6900° A, characterizing the presence of a malignant tumor.

2. The apparatus of claim 1 wherein the light source means is a mercury lamp with a set of ultraviolet filters.

3. The apparatus of claim 1 wherein said light source means is an ultraviolet laser selected from the group consisting of Nitrogen laser, a Krypton laser, an Xenon laser, and an ultraviolet excimer laser.

4. The apparatus of claim 1 wherein the end of the fiber optic bundle transmitting the near-ultraviolet light that is nearest the tumor and the incident end of the fiber optic bundle transmitting the generated intrinsic fluorescent light form a 45-degree angle with respect to each other.

5. The apparatus of claim 1 wherein the ultraviolet light means provides light of 3400° A±200° A.

6. The apparatus of claim 1 wherein the optical fibers for transmitting the near ultraviolet light to the surface of the tumor are made of quartz.

7. An apparatus for the visual diagnosis of malignant tumors comprising:
   (a) means for generating near ultraviolet light having a frequency range of 3000° A to 4000° A;
   (b) light transmission means composed of a bundle of optical fibers for transmitting the ultraviolet light to the surface of a tumor in order to stimulate intrinsic fluorescent light emission from said tumor;
   (c) further light transmission means composed of a second bundle of optical fibers having an incident end and an efferent end for transmitting the stimulated intrinsic fluorescent light emitted by the tumor wherein the presence of red light having a frequency of 6000° A to 6900° A emerging from the efferent end of said second bundle of optical fibers indicates the presence of a malignant tumor.

* * * * *

UNITED STATES PATENT AND TRADEMARK OFFICE
CERTIFICATE OF CORRECTION

PATENT NO. : 4,957,114

DATED : September 18, 1990

INVENTOR(S) : Kun ZENG, Jinrong WU, Sen Yang, Zhenfen YU and Jiude ZHU

It is certified that error appears in the above-identified patent and that said Letters Patent is hereby corrected as shown below:

Drawing

In Fig. 1, please reverse the direction of the arrow corresponding with optical fiber 4, so as to point in an upward direction from the test tissue 3 towards the color resolution means 5.

Signed and Sealed this

Eighth Day of December, 1992

*Attest:*

DOUGLAS B. COMER

*Attesting Officer*      *Acting Commissioner of Patents and Trademarks*